(12) United States Patent
Brown

(10) Patent No.: US 10,668,155 B2
(45) Date of Patent: *Jun. 2, 2020

(54) HYALURONIC ACID STABILIZER

(71) Applicant: Karen K. Brown, Parkville, MO (US)

(72) Inventor: Karen K. Brown, Parkville, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/917,919

(22) Filed: Mar. 12, 2018

(65) Prior Publication Data

US 2018/0200371 A1     Jul. 19, 2018

Related U.S. Application Data

(63) Continuation of application No. 14/995,325, filed on Jan. 14, 2016, now Pat. No. 9,913,906, which is a continuation of application No. 13/874,031, filed on Apr. 30, 2013, now Pat. No. 9,238,071.

(60) Provisional application No. 61/789,928, filed on Mar. 15, 2013, provisional application No. 61/640,904, filed on May 1, 2012.

(51) Int. Cl.

| | |
|---|---|
| *A61K 47/12* | (2006.01) |
| *A61K 31/728* | (2006.01) |
| *A61K 9/00* | (2006.01) |
| *A61K 47/02* | (2006.01) |
| *A61K 9/06* | (2006.01) |
| *C08L 5/08* | (2006.01) |
| *C08B 37/08* | (2006.01) |
| *A61K 8/73* | (2006.01) |
| *A61K 8/04* | (2006.01) |
| *A61K 8/365* | (2006.01) |
| *A61K 9/08* | (2006.01) |
| *A61Q 11/00* | (2006.01) |
| *A61Q 19/00* | (2006.01) |
| *A61K 47/22* | (2006.01) |
| *A61K 47/46* | (2006.01) |

(52) U.S. Cl.
CPC .............. *A61K 47/12* (2013.01); *A61K 8/042* (2013.01); *A61K 8/365* (2013.01); *A61K 8/735* (2013.01); *A61K 9/0014* (2013.01); *A61K 9/06* (2013.01); *A61K 9/08* (2013.01); *A61K 31/728* (2013.01); *A61K 47/02* (2013.01); *A61Q 11/00* (2013.01); *A61Q 19/00* (2013.01); *C08B 37/0072* (2013.01); *C08L 5/08* (2013.01); *A61K 47/22* (2013.01); *A61K 47/46* (2013.01); *A61K 2800/524* (2013.01)

(58) Field of Classification Search
None
See application file for complete search history.

(56) References Cited

PUBLICATIONS

Miyake, JP 2002 09950A, Jan. 29, 2002, machine translation.*
Ai, CN 101914225 A, Dec. 15, 2010, English abstract only.*

\* cited by examiner

*Primary Examiner* — Layla D Berry
(74) *Attorney, Agent, or Firm* — Barnes & Thornburg LLP

(57) ABSTRACT

An embodiment of the present disclosure provides a composition that comprises hyaluronic acid, or its salt or derivative thereof, and an antimicrobial agent, such as zinc citrate, that does not degrade the hyaluronic acid molecule.

19 Claims, No Drawings

HYALURONIC ACID STABILIZER

RELATED APPLICATIONS

The present application is a continuation application of U.S. patent application Ser. No. 14/995,325, filed on Jan. 14, 2016, entitled "Hyaluronic Acid Stabilizer" (now U.S. Pat. No. 9,913,906, issuing on Mar. 13, 2018), and is related to and claims priority to U.S. patent application Ser. No. 13/874,031, filed on Apr. 30, 2013, entitled "Hyaluronic Acid Stabilizer," (now U.S. Pat. No. 9,238,071, issued on Jan. 19, 2016) and is related to and claims priority to U.S. Provisional Patent Application Ser. No. 61/789,928, filed on Mar. 15, 2013, entitled "Hyaluronic Acid Stabilizer" and to U.S. Provisional Patent Application Ser. No. 61/640,904, filed on May 1, 2012, entitled "Hyaluronic Acid Stabilizer." To the extent not included below, the subject matter disclosed in these provisional and utility patent applications is hereby expressly incorporated into the present application by reference.

TECHNICAL FIELD AND SUMMARY

The present disclosure relates to hyaluronic acid compositions, and more particularly to hyaluronic acid compositions that inhibit or eliminate growth of bioburden using natural additives without substantially degrading the hyaluronic acid polymer.

The present disclosure also includes a process for chemical sterilization of hyaluronic acid ("HA") in an aqueous base such as a liquid or gel, wherein an antimicrobial agent significantly reduces/inhibits the growth or eliminates the bioburden found in HA while not substantially degrading the HA polymer (i.e., break the HA down into lower molecular weight components). The present disclosure is further directed to additives, including dietary or nutritional supplements, which may be added to HA that will not substantially degrade the HA polymer or breakdown the molecular weight as measured by a decrease in viscosity. The present disclosure is still further directed to additives that protect the HA from breakdown even when antimicrobial agents, compounds, chemical, dietary, natural, or nutritional supplements are added that may otherwise breakdown the HA polymer. Additives may also function to reduce the bioburden and act as an antimicrobial agent.

An illustrative embodiment of the present disclosure provides a composition that comprises hyaluronic acid, or its salt(s) or derivative(s) thereof, and zinc citrate (or other zinc compounds including zinc sulfate, zinc nitrate, or zinc gluconate).

The above and other illustrative embodiments of the composition may further comprise: the zinc citrate functions to reduce microbial load, prevents contamination of said composition, and does not substantially reduce the molecular weight of the hyaluronic acid; the hyaluronic acid, or its salt or derivative thereof, may function as a supplement for mammals to improve conditions selected from the group consisting of at least one of skin health, eye health, tooth health, gum health, behavioral conditions selected from the group consisting of at least one of ADHD, autism and ADD, immune system health, muscle health or pain and joint health or pain; the zinc citrate is in a form selected from the group consisting of at least one of a monohydrate, a dihydrate and a trihydrate; a formulation wherein the zinc citrate has a concentration from about 0.0001% to about 50%; the composition does not undergo a reduction in original viscosity by more than about 50% over about 6 months as measured by rhelogic viscosity in centepois; the composition demonstrates microbial growth of less than about 10 colony-forming units on blood agar plates over its shelf life of at least 6 months; the hyaluronic acid, or its salt or derivative thereof, has a molecular weight of about 100,000 Daltons to about 3 million Daltons; the hyaluronic acid, or its salt or derivative thereof, has a molecular weight of about 100,000 Daltons to about 10 million Daltons; and the zinc citrate functions as an antimicrobial agent.

Another illustrative embodiment provides an aqueous-based composition comprising about 0.001% to about 5% by weight hyaluronic acid, or its salt or derivative thereof, having a molecular weight of about 100,000 Daltons to about 3 million Daltons; and about 0.0001% to about 50% by weight zinc citrate.

The above and other illustrative embodiments of the composition may further comprise: the zinc citrate is selected from the group consisting of monohydrate, dihydrate and trihydrate; the aqueous-based composition formulation demonstrates microbial growth of less than about 10 colony-forming units over about 6 months; the aqueous-based composition does not undergo a reduction in original viscosity by more than about 50% over about 6 months as measured by rhelogic viscosity in Centepois; the hyaluronic acid, or its salt or derivative thereof, has a molecular weight of about 100,000 Daltons to about 3 million Daltons; the hyaluronic acid, or its salt or derivative thereof, has a molecular weight of about 100,000 Daltons to about 10 million Daltons; and the aqueous-based composition is selected from the group consisting of a liquid, gel, cream, liquid-gel, semi-solid, and ointment.

Another illustrative embodiment of the present disclosure provides an aqueous-based composition comprising: about 0.001% to about 5% by weight hyaluronic acid, or its salt or derivative thereof, and about 0.0001% to about 50% by weight zinc citrate; wherein the composition has an original viscosity as measured at a time 0 by a rhelogic viscosity method; and wherein the original viscosity does not reduce more than about 50% over about 6 months as measured by the rhelogic viscosity method.

The above and other illustrative embodiments of the composition may further comprise: the aqueous-based composition demonstrates microbial growth of less than about 10 colony-forming units over about 6 months; the hyaluronic acid, or its salt or derivative thereof, has a molecular weight of about 100,000 Daltons to about 3 million Daltons; the hyaluronic acid, or its salt or derivative thereof, has a molecular weight of about 100,000 Daltons to about 10 million Daltons; and the aqueous-based composition is selected from the group consisting of a liquid, gel, cream and ointment.

Unless otherwise defined, all technical and scientific terms used herein have the same meaning as commonly understood by one of ordinary skill in the art to which this disclosure belongs. Suitable methods and materials are described below, although methods and materials similar or equivalent to those described herein may also be used in the practice or testing of the subject matter of the present disclosure. All publications, patent applications, patents, and other references mentioned herein are incorporated by reference in their entirety. In case of conflict, the present specification, including definitions, will control. In addition, the materials, methods, and examples herein are illustrative only and not intended to be limiting.

Additional features and advantages of the disclosed compositions and methods will become apparent to those skilled in the art upon consideration of the following detailed description of the illustrated embodiment exemplifying the best mode of carrying out the disclosed compositions and methods as presently perceived.

DETAILED DESCRIPTION

Hyaluronic acid, or its salt or derivative thereof, also known as sodium hyaluronate, hyaluronate sodium and hyaluronan (referred collectively herein as "HA"), is a glycosaminoglycan that is naturally found in mammals. HA is generally a large polymer made up of repeating units of N-acetyl-glucosamine and D-glucuronic acid. HA's molecular weight can vary from a few thousand Daltons to more than 10 million Daltons. HA is also well known to be polydisperse. (David C. Armstrong and Michael R. Johns, *Culture Conditions Affect the Molecular Weight Properties of Hyaluronic Acid Produced by Streptococcus zooepidemicus*, Applied and Environmental Microbiology, July 1997, p. 2759-2764; and James H. Kimura, Philip Osdoby, Arnold I. Caplan, and Vincent C. Hascall, *Electron Microscopic and Biochemical Studies of Proteoglycan Polydispersity in Chick Limb Bud Chondrocyte Cultures*, The Journal of Biological Chemistry Vol. 253, No. 13, Issue of July 10, pp. 4721-4729, 1978.)

Recently, HA has become known to inhibit inflammation; improve joint health, skin and vision; relieve symptoms of fibromyalgia, pain, itching, arthritis (osteoarthritis and rheumatoid arthritis), gastritis, colitis, esophagitis, bronchitis, sore throat, tonsillitis, tendonitis, swollen and painful joints, bruised tissue, cramped muscles, inflamed muscles, tired feet, fibromyalgia, headaches including migraines, pancreatitis, vaginitis, hemorrhoids, sunburn, heat burns, TMJ, dental pain, gingivitis, dental caries, dental pain, post surgical pain, menstrual pain, anaphylaxis, pain prior to and during childbirth, allergies, asthma, itching associated with allergies and hypersensitivity, poison ivy, psoriasis, Attention Deficit Hyperactivity Disorder (ADHD), Attention Deficit Disorder (ADD), autism, plaque formation associated with heart disease and stroke, increased degradation of spinal nerves post spinal cord injury, adhesion formation post surgery, scar formation post surgery, lack of wound healing, decubitus ulcers, irritation of nerve bundles, ganglion formation, heart disease, Alzheimer's disease, HIV, cancer, Diabetes, acne, wrinkles, and even hair loss.

HA is found almost everywhere throughout the mammalian body, and is particularly concentrated in the joint fluid, skin, and vitreous humor of the eyes. There is also HA in the brain and cerebral spinal fluid, heart, around the heart sac, and in the lungs.

About one-third of the body's total HA is replaced every day. (Fraser, J. R., T. C. Laurent, and U. B. Laurent, *Hyaluronan: its nature, distribution, functions and turnover*, J. Intern. Med. 242:27-33 1997; and Todd D. Camenisch and John A. McDonald *Hyaluronan Is Bigger Better?* Am. J. Respir. Cell Mol. Biol., Vol. 23, pp. 431-433, (2000).) As HA breaks down it turns into glucosamine which is believed to stimulate production of endogenous HA by the body. (Conte, A. N. Volpi, L. Palmieri, I. Bahous, and G. Ronca, *Biochemical and Pharmokinetic Aspects of Oral Treatment with Chondroitin Sulfate*, Arzneim.-Forsch. (Drug Res.) 45(8) 918-925 (1995); McCarty, M. F., A. L. Russell, and M. P. Seed, *Sulfated Glucosaminoglycans and Glucosamine may Synergize in Promoting Synovial Hyaluronic Acid Synthesie*, Medical Hypothesis 54: 798-802, 2000; and McCarty, M. F., *Enhanced Synovial Production of Hyaluronic Acid May Explain Rapid Clinical Response to High-dose Glucosamine in Osteoarthritis*, Medical Hypothesis 50:507-510 (1998).)

In addition there are three genes in the body that naturally produce HA. HAS1 and HAS2 produce HA with a molecular weight $\geq 2.0 \times 10^6$, whereas HAS3 produces HA in the molecular weight range of $2\text{-}3 \times 10^5$. (Smith and Ghosh, Rheumatol Int, 1987, 7:113-122) Because HA is continually catabolized (broken down) in the body, HA needs constant replenishing. (Holmes, Michael W A, Michael T. Bayliss, and Helen Muir, *Hyaluronic acid in human articular cartilage*, Biochem J. 250, 435-441 (1988); and Jérémie Sellam & Francis Berenbaum, *The role of synovitis in pathophysiology and clinical symptoms of osteoarthritis*, Nature Reviews Rheumatology 6, 625-635 (November 2010).) For purposes of this disclosure "break down" or "degrade" means the molecular weight of HA lowers. Thus, a repetitive cycle occurs—the body breaks down HA into glucosamine which stimulates new HA which breaks down into glucosamine again and repeats the process. When the body is operating optimally, it is constantly producing high molecular weight HA via this process. As mammals age, the ability of the body to replenish the high molecular weight HA decreases, making supplementation more important. If the body is unable to produce sufficient amounts of HA, or if higher concentrations are needed to relieve the aforementioned maladies, HA can be supplemented. HA may be supplemented via oral, mucosal or topical administration to mammals, including humans, dogs, horses, cats and all other animals.

HA in the body binds to several receptor sites, one of which is CD44. Other substances such as chondroitin sulfate also bind to CD44, but HA's bond is believed to be about 100 times stronger than that of chondroitin sulfate. (Aruffo, et al., 1990. Cell Vol 61, Issue 7, 1303-1313.) The CD44 and RHAMM receptors are found on most organs of the body except the stomach and intestines. This is notable because HA is available in pill form. If the pill is swallowed (and not absorbed in the mouth, other mucous membranes or the trachea), there is no appropriate receptor sites in the stomach to absorb the HA, making the pill's efficacy questionable. Furthermore, capsules, like pills, are designed to dump product into the stomach—a highly acidic environment. Instead of absorbing the HA, stomach acid degrades it into fragments. With no CD44 or RHAMM receptors, HA cannot be absorbed and delivered where needed. Oral or mucosal delivery can still be effective, so long as the delivery mechanism is designed so the HA absorbs in the mouth, other mucous membranes, or trachea. There are sufficient CD44 receptor sites at these locations to absorb HA.

Liquid HA compositions may accomplish this task. Because the liquid HA is compatible with the lining of the bucal cavity, it is readily absorbed within the mouth. The mucous membranes also contain a significant number of CD44 receptor sites that bind specifically to HA. These membranes also allow rapid absorption and effectiveness as noted in U.S. Pat. No. 8,003,782, the contents of which are expressly incorporated herein by reference.

As more is learned about HA, however, it is demonstrating itself as having varying characteristics. On one hand, high molecular weight HA demonstrates effectiveness, acting both as a supplement and to pharmacologically improve joint function, skin conditions and rashes, eye conditions, diseases and other conditions related to the body's inflammatory processes. High molecular weight HA is also used to lubricate joints and reduce inflammation. HA is effective having at least one fraction that is greater than 1,000,000

Daltons as demonstrated in U.S. Pat. No. 8,003,782, for example. High molecular weight molecule HA is known to have anti-inflammatory effect in vivo as well. As such, it believed to be useful to treat and relieve many diseases or conditions related to inflammation. (Ialenti, A. and M. Di Rosa, *Hyaluronic Acid Modulates Acute and Chronic Inflammation*, Agents Actions, 43, 44-47 (1994).)

On the other hand, low molecular weight HA has been reported to have radically different properties, the most significant of which is that it may be pro-inflammatory, signaling production of inflammatory cytokines which results in pain. The dividing line between anti-inflammatory and pro-inflammatory HA properties is believed to be about 500,000 Daltons. (See Camenisch, T D and J A McDonald, *Hyaluronan: Is bigger better?* Am J. Respir. Cell Mol. Biol. 23: 434-433 (2000).) Therefore, for therapeutic use, maintaining high molecular weight HA, particularly for use as a supplement for the mammalian body is important. Put simply, high molecular weight HA is naturally produced in the body and supplementing it with additional high molecular weight HA may have numerous benefits.

All HA is polydisperse. (David C. Armstrong and Michael R. Johns, *Culture Conditions Affect the Molecular Weight Properties of Hyaluronic Acid Produced by Streptococcus zooepidemicus*, Applied and Environmental Microbiology, July 1997, p. 2759-2764; and James H. Kimura, Philip Osdoby, Arnold I. Caplan, and Vincent C. Hascall, *Electron Microscopic and Biochemical Studies of Proteoglycan Polydispersity in Chick Limb Bud Chondrocyte Cultures*, The Journal of biological Chemistry Vol. 253, No. 13, Issue of July 10, pp. 4721-4729, 1978.) In other words, raw HA material contains multiple molecular weight fractions, not all high and not all low. For purposes of this disclosure the term "molecular weight" means the average molecular weight, such as the molecular weight reported on a Certificate of Analysis from a HA manufacturer, for example. Such molecular weights are believed to be the molecular weights when the HA is initially manufactured and supplied to a formulator (i.e., an individual or company that develops a product formulation).

Determining HA's molecular weight may be achieved via several methods. An empirical test for liquid phase HA is visually accessing its viscosity. Although not precise by any means, a thick, viscous HA ($\geq 0.4\%$) is indicative of a higher molecular weight, whereas thin, watery HA is indicative of low molecular weight. Intrinsic viscosity is a method by which the viscosity of HA can be more precisely determined. The latter method is time-consuming. A faster method which measures the rheologic viscosity can be correlated to Intrinsic viscosity. Most providers of raw material HA utilize one of these methods for determining and reporting the molecular weight as the average molecular weight for HA. Additional methods include sedimentation equilibrium centrifugation, gel permeation chromatography (GPC), also called size exclusion chromatography (SEC) coupled with a UV detector, SEC coupled with a light scattering detector (SEC-MALS), electrophoresis and Near Infrared Spectroscopy (NIR). None of the methods provide exact molecular weight measurements. All have positive and negative attributes. The most critical factor in molecular weight determination is to be consistent and use the same method throughout evaluation and testing of a product from purchase, through formulation, manufacture and demonstration of stability or shelf life. By using a consistent method for monitoring the HA stability (lack of degradation) can be determined. High molecular weight HA fractions may be made in a variety of ways, such as harvesting it from rooster combs, the trachea or umbilical cords of cattle, or through microbial fermentation. The latter is a preferred method since it may exclude animal origin components. Purity issues, allergic reactions, and disease transfer may occur from HA derived from animals. In contrast, microbial fermentation harvests HA that is formed around various types of bacteria, yeast or fungi. It is then purified away from the organism. A description of this process may be found in U.S. Pat. No. 4,808,576.

High molecular weight HA, even when produced through microbial fermentation, is susceptible to contamination with microorganisms such as bacteria, mold/fungi and yeast over time. Hereinafter, any such contamination will be referred to here as bioburden. Some batches may initially contain less than 10 microorganisms per gram (in the powder or crystalline form), others less than 100 microorganisms per gram, and still others less than 1000 microorganisms per gram. Liquid HA is more difficult to manufacture and is, therefore, usually more expensive because it needs to have the bioburden controlled such that the HA does not develop gross contamination. A bioburden of less than 10 colony forming units (CFU) per mL demonstrates control of the microbial growth. However, it is preferable to have less than 1 CFU/mL to be sure that there will not be gross contamination over time. If left untreated, these microorganisms can grow and break down HA's molecular weight. As indicated previously, when HA is broken down or degraded into its smaller fragments (e.g., less than 500,000 Daltons), it may have undesirable or no effects on the body rather than desirable effects. This is in addition to the bioburden which may itself be unhealthy.

To rid HA of bioburden it must either be pre-sterilized or include an antimicrobial agent. The term antimicrobial agent is defined as an additive that reduces the bioburden in the HA to less than 10 CFU/mL when the HA formulation is stored at room temperature over a period of at least 6 months. The antimicrobial agent maintains the molecular weight (as measured by rheologic viscosity in Centipoise) of the HA molecule or protects the HA molecule from being broken down. Various methods are currently used to try to prevent or delay growth of microbial contaminants. These various methods may be more or less successful in reducing microbial growth in HA formulations.

For purposes of this disclosure, the antimicrobial agent is added before microbial growth can occur. Sterilizing means that the bioburden contained in the HA powder is substantially killed when mixed with the antimicrobial agent. Adequate chemical sterilization or inhibition of microbial growth is demonstrated by applying 1.0 to 2.0 mL of the HA containing the antimicrobial agent to each of three blood agar plates, incubating them for at least 5 days at 35-38° C. plus at least 7 days at room temperature (20-25° C.) wherein there are fewer than 10 colonies on any of the three plates. Preferably, there are fewer than 2 colonies on any one plate. More preferably, there are no colonies on any of the three plates. The term inhibitory means that the growth of the bioburden contained in the HA powder is inhibited when the powder is added to a liquid base, so that the organisms will not grow when inoculated onto blood agar plates as described previously. Breaking down the HA molecule means that the molecular weight as measured, for example, by rheologic viscometry is not reduced by more than 50% over a period of three months. Rheologic viscosity is measured in Centipoise (cP) using a Brookfield LVIII Viscometer. Break down of the HA molecule means degradation of the HA polymer as demonstrated by a reduction in the rheologic viscosity of more than 50% within a three month time period. Rheologic viscosity may be measured in Centipoise (cP) using a Brookfield LVIII Viscometer.

Unfortunately, most antimicrobial agents also degrade the HA molecule in a manner similar to that produced by a bioburden. For example, HA is heat sensitive, so heat sterilization breaks it down. U.S. Pat. No. 5,621,093 describes a method of steam sterilizing solid HA. Though reducing bioburden, this method is believed to degrade HA's molecular weight, even if not as much as heat sterilizing the liquid form or using dry heat sterilization. Likewise, U.S. Pat. No. 6,891,035 describes a method of autoclaving polysaccharides, including HA, in liquid form to reduce contamination. Again, this method is believed to break down the molecular weight as measured by a reduction in viscosity. The inventors claim, however, that the degradation is acceptable for their use.

HA is also sensitive to irradiation. This method of sterilization breaks down the polymer depending on time and amount of irradiation. (See Kuo, J. W., *Practical Aspects of Hyaluronan Based Medical Products*, CRC Press, pp 40-41 2006.) HA loses molecular weight as evidenced by a loss in viscosity. Freeze drying, ultrasonic treatment and the addition of chemicals such as hydrogen peroxide, ascorbic acid, strong acids and strong bases are also known to degrade HA. (See Id. at pp 34-42.)

Furthermore, lower molecular weight HA (or HA fractions) is a less expensive starting material than higher molecular weight HA. By comparison, high molecular weight HA (>1,000,000 Daltons) is more difficult to prepare, particularly in an aqueous solution that is >0.4% (4 mg/mL). Some products, nutritional and dietary supplements and drugs, may use lower molecular weight HA that is mixed with a food-grade thickening agent, such as carbopol or xantham gum. This makes the product appear viscous indicative of high molecular weight HA when, in fact, it's only the additives responsible for the viscosity. The lower molecular weight HA added remains the ineffective lower molecular weight HA. HA can actually degrade in these formulations but the degradation won't be detected because the thickening agents mask the degradation.

Antimicrobial agents are often added to HA to control bacterial and fungal growth. Antimicrobial agents approved for use by the Food and Drug Administration (FDA) include potassium sorbate, citric acid, potassium or sodium citrate, ethylenediaminetetraacetic acid (EDTA), and vitamin C (ascorbic acid, sodium ascorbate or potassium ascorbate). Most of these are minimally effective as antimicrobial agents when the liquid carries a bioburden that must be overcome. Of greater concern, however, is what effect these antimicrobial agents have on the HA molecule itself. Such additives have been found to degrade HA. Citric acid at 0.1%, for example, breaks down HA in a matter of months. Similarly, EDTA breaks down HA. Sodium or potassium sorbate at different percentages—0.1% or 0.2% break down HA. There are additives that do not break down HA including methyl paraben, propyl paraben and propylene glycol. The problem is that these additives tend to be unacceptable to the holistic/homeopathic or natural health food or supplement markets because they are considered artificial antimicrobial agents that may have deleterious health effects. These markets tend to require all natural components. Interestingly, most of the natural components tested are either not effective enough to inhibit the bioburden already found in HA or they degrade the HA molecule. Surprisingly, we have discovered natural components that can not only inhibit microbial growth but also do not degrade the HA molecule and stabilize HA formulations. In addition to these additives, many formulators prepare complex mixtures of aqueous-based compositions that contain supplements other than HA. For example, they may add vitamins (e.g., omega 3, Vitamin C, Vitamin E or tocopherols), muscle and joint support products (e.g., grapeseed extract, glucosamine (sulfate or HCl), methyl sulfonyl methane (MSM), chondroitin sulfate) or other types of supplements. Many of these components may degrade the HA molecule as well.

In order to evaluate antimicrobial agents to determine their long-term effect on the HA molecule, a 1.0% HA solution was prepared by adding 1.0 g of powdered HA obtained from HTL (SARL JAVERNE factory, La Boitardière 35133, FOUGERES, FRANCE) to 100 mL of sterile distilled water. The starting molecular weight of the HA, according to the Certificate of Analysis, was 1.5 million Daltons. Additives were then added directly to the water prior to adding the HA. The additives (natural antimicrobial agents or supplements) were not pre-sterilized prior to addition. The solutions were shaken and allowed to stand at room temperature until a homogenous gel was observed. Dissolution required about 2-3 days with intermittent mixing. As soon as the preparations were dissolved, the starting viscosity was determined using a Brookfield LVIII Viscometer that had been validated against Intrinsic Viscosity and GPC (SEC). A molecular weight estimate can be made from these data. However, all data presented herein show the viscosity as measured in Centipoise (cP) rather than the molecular weight extrapolated from the viscosity reading. Results of this investigation are shown in Table 1.

TABLE 1

Six month stability of HA gels containing various antimicrobial agents as measured by rheologic viscosity

| | Viscosity in Centipoise (cP) | | | | | |
|---|---|---|---|---|---|---|
| Additive | Day 0 | 1 Mo | 2 Mo | 4 Mo | 6 Mo | Comments |
| None | 18329 | ND | ND | ND | 17899 | Clear |
| 0.1% alpha tocopherol succinate | 18329 | 11624 | ND | 5479 | 3159 | Oily - not dissolved, not a good formulation |
| 0.1% potassium sorbate | 14769 | 6265 | 4332 | 3692 | 786 | Turned yellow over time |
| 0.1% citric acid | 18329 | 10690 | 5925 | 2586 | 252 | Very thick at start then got slimy |

Table 1 indicates that all of the additives tested degrade the HA. The HA containing no additives was stable for the six month time period maintaining a viscosity of around 18,000 cP. The HA containing only 0.1% potassium sorbate, 0.1% citric Acid, or 0.1% alpha tocopherol succinate showed significant reductions in viscosity indicating degradation of the HA polymer. This would indicate that these additives will not be acceptable to use in liquid, gel, or cream formulations without addition of a stabilizer.

To confirm these results, further testing was performed to determine whether the preparations containing the potassium sorbate, citric acid, or alpha tocopherol contained a bioburden and the microorganisms produced the degradation. In this experiment, the HA was prepared as previously described, except that a known acceptable antimicrobial system was added at the same time as the test additives were added. The acceptable antimicrobial system contained propylene glycol in which was dissolved methyl paraben and propyl paraben (PMP). In previous experiments it has been determined that PMP does not degrade the HA polymer and serves as an exceptional antimicrobial system. It is accepted by the Food and Drug Administration (FDA) and has been incorporated into oral HA formulations for years. PMP has produced no adverse reactions in mammals including humans, dogs, and horses. Many people who take supplements, however, do not want them to contain propylene glycol or parabens which is why this disclosure relates to alternative natural antimicrobial agents and additives. The control was 1% HA containing 1% PMP alone. All test formulations contained this base amount of PMP. Additional additives included 0.1% citric acid, 0.15% EDTA, 0.1% potassium sorbate or 0.2% potassium sorbate.

TABLE 2

Thirty-four month stability of HA gels containing PMP along with various antimicrobial agents as measured by rheologic viscosity

| | Viscosity in Centipoise (cP) | | | |
|---|---|---|---|---|
| Additive | Day 0 | 6 Mo | 34 Mo | Comments |
| 1% PMP alone | 12517 | 16236 | 11850 | Clear |
| 1% PMP + 0.1% citric acid | 8864 | 200 | 0 | Very thick at first -- sticky, turns slimy later |
| PMP + 0.15% EDTA | 800 | 560 | 0 | Clear |
| PMP + 0.1% Potassium sorbate | 1292 | 1120 | 0 | Turns dark yellow -- degraded |
| PMP + 0.2% Potassium sorbate | 1080 | 1040 | 880 | Turns dark yellow - degraded |

As shown in Table 2, the formulation containing PMP alone (Control) maintained its viscosity for a period of 34 months. All of the other formulations, however, lost viscosity indicating that the additive components produced degradation of the HA polymer. Day 0 represents the first viscosity test conducted. This was approximately two weeks after the formulations were prepared. During that time, all of the formulations except the one containing only PMP lost viscosity during this dissolution time. All formulations were tested for the presence of bioburden by plating 1.0 mL onto each of three blood agar plates. No microbial growth (bacterial or fungal) was present on any of the plates at the end of 34 months. This indicates that the degradation was not produced by microbial contamination.

A repeat study was performed using a different HA raw material at a lower molecular weight. This HA had a stated molecular weight (on the Certificate of Analysis) of around 1.0 kDa. The formulations were prepared as described above (containing the 1% PMP added as a known effective antimicrobial agent). In this case only the 0.1% EDTA, 0.1% potassium sorbate and 0.2% potassium sorbate were tested. The results are shown below in Table 3.

TABLE 3

Ten month stability of HA gels containing various antimicrobial agents as measured by rheologic viscosity

| | Viscosity in Centipoise (cP) | | | |
|---|---|---|---|---|
| Additive | Day 0 | 3 MO | 10 Mo | Comments |
| 1% PMP Alone | 3280 | 2840 | 2997 | Clear |
| 1% PMP + 0.15% EDTA | 3200 | 1760 | 800 | Clear |
| 1% PMP + Potassium Sorbate 0.1% | 2400 | 2080 | 1280 | Turning yellow by 10 mo |

TABLE 3-continued

Ten month stability of HA gels containing various antimicrobial agents as measured by rheologic viscosity

| | Viscosity in Centipoise (cP) | | | |
|---|---|---|---|---|
| Additive | Day 0 | 3 MO | 10 Mo | Comments |
| HA in PMP Water + Potassium Sorbate 0.2% | 2300 | 1880 | 1080 | Turning yellow by 10 mo |

This test only ran for 10 months as it was obvious, as shown above, that the same degradation was occurring. All formulations were tested at the end of the 10 month test period for the presence of microbial contamination by plating at least 1.0 mL from each formulation onto each of three blood agar plates. All plates were free of microbial growth. Therefore, the HA degradation was related to the additives, not to microbial contamination. The PMP alone did not demonstrate significant degradation of the HA.

It is interesting to note that when citric acid is added to the HA formulation(s) the preparation becomes initially extremely viscous, almost to the point of producing a solid. After a few weeks, the citric acid formulations became very slick and it was obvious that the viscosity was dramatically reduced. The pH of the citric acid formulations were not significantly different from the pH of the HA formulation containing PMP alone. The degradation was, therefore, not related to the pH of the citric acid formulations. Although the potassium sorbate solutions did not show the high viscosity upon initial preparation, they did degrade rapidly, even though the pH of these solutions also remained similar to that of the HA formulations containing PMP. It is also noted that the potassium sorbate formulations developed a yellow coloration with time as well as an unacceptable taste. The yellow color is an indication of carmelization (breakdown of sugars which are the components of HA) and confirmed the degradation of the HA. This has been noted with formulations containing other additives that rapidly degrade HA such as Vitamin C. In sum, these additives failed to qualify as a sufficient antimicrobial agent for HA.

These data indicate that the HA polymer is a fragile molecule. Any additive should not be included in a HA formulation without considering its effect on the HA molecule in addition to its effect on bioburden, or primary function. Although scientists have reported this polymer fragility it is not generally appreciated in the supplement marketplace. However, this supplement market does understand the importance of high molecular weight HA As demonstrated, this lack of appreciation and understanding of 1) the necessity to protect the HA molecule from degradation by additives or antimicrobial agents; 2) how HA's molecular weight affects efficacy; and 3) how the modes of HA delivery need to ensure that it reaches a proper receptor, means that some HA-containing products may or may not perform adequately. This is further complicated by the dichotomy between adding constituents that reduce contamination with their side-effect of degrading HA. It is, therefore, evident that creating a HA composition that is both efficacious and has a reasonable shelf life (i.e., not dangerously contaminated with a bioburden) is easier said than done.

This present disclosure reconciles these problems by disclosing natural antimicrobial agents that, when combined with HA, form a composition that does not appreciably break down the HA's molecular weight while controlling bioburden. These antimicrobial agents also act as sterilizing or inhibiting agents when added to HA in liquid formulations. They also do not significantly degrade a HA polymer.

It is appreciated that the term "composition" as used herein means the nature and proportions of the constituents comprising a chemical compound. The meaning encompasses both the composition's formulation, as well as its resultant composition.

An aspect of this disclosure includes a process of chemical sterilization of HA in any type of non-solid form that produces a chemical sterilizing or microbial inhibitory effect that does not break down or degrade the HA molecule. In addition, this disclosure relates to adding an antimicrobial agent that also protect the HA molecule from breakdown due to additives that would ordinarily breakdown the polymer if the agents were not present.

The following constituents are believed acceptable additives that do not degrade HA alone or in combination: chondroitin sulfate (CS), methyl sulfonyl methane (MSM), grapefruit seed extract, zinc citrate, proline, calcium propionate, sodium or potassium benzoate, 1,2-propanediol (propylene glycol), methylparaben, propylparaben and Citracidal™, radish root extract, Leucidal™, Natamycin, Nisin, beta-alanine and carnosine.

The following are also effective as antimicrobial agents, alone or in combination zinc citrate (or its salt including zinc sulfate, zinc nitrate, or zinc gluconate) grapefruit seed extract, calcium propionate, sodium or potassium benzoate, 1,2-propanediol, methyl paraben, propyl paraben, raddish root extract, Leucidal™ and Citricidal™. An illustrative embodiment includes a composition that comprises HA and zinc citrate. The zinc citrate functions to reduce microbial load and prevent contamination while not substantially reducing the molecular weight of the HA. In addition, the zinc citrate may function to support the immune system and improve the skin as well as to support gum health by removing calculus from the teeth. In another embodiment the composition may include a formulation of about 0.001% to about 5% by weight HA having a molecular weight of about 100,000 Daltons to about 3 million Daltons, and about 0.0001% to about 50% by weight zinc citrate. The zinc citrate may be in a form selected from the group consisting of at least one of a monohydrate, a dihydrate, and a trihydrate. The formulation of the composition may include zinc citrate at a concentration from about 0.0001% to about 50%. The resulting composition may not undergo a reduction in original viscosity by more than about 50% over about 6 months as measured by rhelogic viscosity in Centepois. Further the composition may demonstrate microbial growth of less than about 10 colony-forming units over a shelf life of at least 6 months. The HA may have a molecular weight of about 100,000 Daltons to about 3 million Daltons, or even to about 10 million Daltons. The composition may also have an original rheologic viscosity as measured at time 0 and that original viscosity does not reduce more than about 50% over about 6 months. It is appreciated that the composition may be a liquid, gel, cream, or ointment.

Another illustrative embodiment includes a composition having HA and two or more additives selected from the group consisting of grapefruit seed extract, Citricidal™ calcium propionate, sodium benzoate, potassium benzoate, magnesium citrate, proline, potassium sorbate, citric acid, raddish root extract, Leucidal™ and 1,2-propanediol; or a combination of zinc citrate and grapefruit seed extract, a combination of zinc citrate and Citricidal™, a combination of zinc citrate and calcium propionate, a combination of zinc citrate, calcium propionate and sodium benzoate, a combination of zinc citrate, calcium propionate and potassium benzoate, a combination of zinc citrate, calcium propionate and grapefruit seed extract, a combination of zinc citrate, calcium propionate and Citricidal™, a combination of zinc citrate and potassium benzoate, a combination of zinc citrate and sodium benzoate, a combination of zinc citrate and 1,2-propanediol, a combination of 1,2-propanediol and methyl paraben, a combination of 1,2-propanediol and propyl paraben, a combination of propyl paraben, 1,2-propanediol, calcium propionate and grapefruit seed extract, a combination of zinc citrate and raddish root extract, a combination of zinc citrate and Leucidal™, and a combination of Citracidal™, 1,2-propanediol, zinc citrate and calcium propionate.

These embodiments may also experience microbial growth of less than about 10 colony-forming units over its shelf life of at least 6 months; not undergo a reduction in original viscosity by more than about 50% over about 6 months as measured by rhelogic viscosity in Centepois; and the HA having a molecular weight of about 100,000 Daltons to about 3 million Daltons or even about 10 million Daltons. It is appreciated that the HA composition may be in any type of non-solid form, including but not limited to liquids, gels, creams and ointments that are useful for parenteral, oral, mucosal, or topical delivery.

The manufacturing process of these embodiments includes dissolving the HA in a liquid, including but not limited to water (sterile, distilled, deionized, purified, WFI or tap), with or without addition of sodium chloride, potassium chloride, sodium phosphate, potassium phosphate, sodium bicarbonate, potassium bicarbonate, other buffering agents or combinations thereof. The HA may be present at any number of concentrations. The starting material for all experiments discussed herein was food grade or cosmetic grade HA from a fermentation or rooster comb source prepared as solution/gel at a concentration from 0.2% to approximately 1.0%. The same results would be expected when using HA derived from any source including, but not limited to bovine trachea, egg membranes, umbilical cords and shell fish. All formulations were prepared using sterile water or sterile water containing physiologic levels of sodium chloride (solution being presterilized). When prepared in very small volumes (approximately 100 mL), the aqueous-based solutions for antimicrobial agent or additive were first tested to determine whether they degraded the HA. If these agents or additives did not degrade the HA, then they were evaluated for their potential to act as an antimicrobial agent in larger volume solutions.

When evaluating additives for potential HA degradation, they were prepared as concentrates and filter sterilized where possible, to assure that they did not add bioburden. Each experiment included a control with no additives. The average molecular weight of the starting HA used for these studies ranged from about 1.0 to 3.0 million Daltons (kDa).

Starting viscosities as measured using a Brookfield LVIII Viscometer that had been validated against GPC (SEC) and Intrinsic Viscosity using protein or HA standards ranged between 1.0 kDa and 3.0 kDa. All high molecular weight samples above 1,000 Centipoise (cP) were evaluated using a #3 spindle at 3.0 rpm at 20° C.±1° C. All medium to low molecular weight samples (<1,000 cP) were evaluated using a #34 spindle at appropriate speeds such that a valid reading could be obtained. The volume of each sample for viscometry was determined by weight and was set at 16.0 g added to a small sample holder that was temperature controlled. All samples were tested upon dissolution and then periodically thereafter for up to 34 months.

After noting the failures of the common antimicrobial agents above, other potential antimicrobial agents and additives were evaluated for their ability to be compatible with liquid HA formulations. These experiments were conducted using HA having a molecular weight of approximately 1.5 million Daltons. Each formulation was prepared in 100 mL quantities of distilled water to which the additive was added whether it was an antimicrobial agent or supplement additive. This water/additive combination was filter sterilized and then a 1.0 g amount of HA was added. The formulations contained no PMP in order to determine whether these additives could be used without an antimicrobial agent. The control was a formulation in which there was no additive. Results are shown below in Table 4.

With respect to the results shown above, it was concluded that the following additives produced no significant degradation of HA and can be used in liquid, gel, cream, or ointment preparations of HA: 1) zinc citrate; 2) proline; and 3) N-acetyl-D-glucosamine. Some of the other additives may be able to be used, but the concentration would have to be lower than was included in this test as the viscosity appeared to stabilize after an initial drop. It is noted that testing was continued for 27 months to determine the stability of each formulation. Because there was a one month period of time between the preparation of the formulations and the first test, it is noted that some significant degradation had already occurred when comparing the viscosity of the additive formulations to that of the control (nothing added) at the time of the first test (1 Mo). The most noteworthy degradation was observed with the addition of calcium ascorbate.

Further evaluation of grapefruit seed extract was undertaken in order to determine whether lower concentrations would be acceptable to add to the HA formulations. Beta alanine and Carnosine were also evaluated in this test. The HA used for this study had a molecular weight of greater than 2.0 Mio Daltons. The procedure was the same as that described above. All formulations were evaluated for a period of 11 months. The results are shown in Table 5.

TABLE 4

Twenty-seven month stability of HA gels containing various antimicrobial agent as measured by rheologic viscosity

| Additive | Viscosity in Centipoise (cP) | | | | | Comments |
| --- | --- | --- | --- | --- | --- | --- |
| | 1 Mo | 2 Mo | 4 Mo | 12 Mo | 27 Mo | |
| NONE | 8638 | 8158 | ND | 12410 | 11122 | Clear |
| 0.05% Zinc Citrate | 11197 | 10157 | 10717 | 11837 | 12197 | Clear |
| 0.3% Zinc Citrate | ND | ND | ND | 13970 | ND | Clear |
| 0.5% Calcium Ascorbate | 279 | 13 | 0 | 0 | 0 | Turned dark yellow |
| 0.05% Proline | 13317 | 12077 | 12637 | 12437 | 12757 | Clear |
| 0.5% Lysine HCl | 4319 | 3759 | 3879 | 3959 | 3439 | Clear |
| 0.2% Magnesium Citrate | 3879 | 3519 | ND | 4266 | 4838 | Clear |
| 0.1% Potassium sorbate + 0.2% Citric Acid | 3599 | ND | 3799 | 3732 | 3732 | Turned yellow |
| 0.01% Copper | 4039 | 3759 | 3239 | 3546 | 3679 | Clear |
| 0.75% glucosamine sulfate | 5585 | 2212 | 1279 | 93 | 79 | Yellow |
| 0.1% Grapeseed Extract | 3252 | 2079 | 1479 | 572 | 519 | Brown |
| 0.03% Grapefruit Seed Extract | ND | ND | ND | 2639 | 2079 | Slightly cloudy |
| N-Acetyl-D-Glucosamine | 10677 | 10277 | 10517 | ND | ND | Clear |

TABLE 5

Eleven month stability of HA gels containing various natural additives as measured by rheologic viscosity

| | Viscosity in Centipoise (cP) | | | |
|---|---|---|---|---|
| Additive | Day 0 | 1 Mo | 4 Mo | 11 Mo |
| PMP | 21195 | 18396 | 16922 | 17438 |
| Grapefruit seed Extract 0.06% | 20116 | 1690 | 160 | ND |
| Grapefruit seed Extract 0.03% | 22088 | 8638 | 1893 | ND |
| Grapefruit seed Extract 0.008% | 22088 | 13157 | ND | 13643 |
| Beta alanine 205 mg/mL | 20078 | 18978 | ND | 18559 |
| Carnosine 205 mg/ml | 19997 | 15836 | ND | 15756 |

Table 5 demonstrates grapefruit seed extract at a concentration of 0.03% and 0.06% showed marked degradation of HA. At 0.008%, however, the amount of viscosity loss was acceptable. Both beta alanine and carnosine did not significantly degrade HA.

With this success, more components were evaluated for their compatibility with HA. The HA used for this next experiment had a molecular weight above 2.0 million Daltons. Again, 100 mL quantities were prepared using sterile distilled water to which was added 1% PMP. HA was added at a concentration of 1.0%. All preparations, including all test preparations, included the 1% PMP to make sure that the bioburden was controlled and that only the additive could be the cause of any HA degradation. The test components were added after the HA was dissolved. Then, each formulation was shaken for 2 days in order to dissolve the HA. The first analyses took place about 2 weeks after the formulations were dissolved. The results are shown in Table 6.

TABLE 6

Eleven month stability of HA gels containing various additives as measured by rheologic viscosity

| | CONC OF | Viscosity in Centipoise (cP) | | | |
|---|---|---|---|---|---|
| ADDITIVES | ADDITIVE | Day 0 | 4 Mo | 5 Mo | 11 Mo |
| PMP | 1.00% | 42300 | 40320 | ND | 33800 |
| Inovapure | 1.00% | 33,200 | 26,080 | ND | 20,320 |
| PMP | 1.00% | | | | |

TABLE 6-continued

Eleven month stability of HA gels containing various additives as measured by rheologic viscosity

| | CONC OF | Viscosity in Centipoise (cP) | | | |
|---|---|---|---|---|---|
| ADDITIVES | ADDITIVE | Day 0 | 4 Mo | 5 Mo | 11 Mo |
| Chondroitin Sulfate | 0.30% | 41,120 | 33,280 | ND | 27,680 |
| PMP | 1.00% | | | | |
| Cynatine | 0.20% | 29,200 | 24,800 | ND | 21,040 |
| PMP | 1.00% | | | | |
| D-glucosamine | 0.30% | 30,122 | 31,440 | 8,800 | 1360 |
| PMP | 1.00% | | | | |
| Potassium Sorbate | 0.20% | ND | 36,800 | 29,600 | 14,000 |
| PMP | 1.00% | | | | |
| Grapeseed Extract | 0.10% | ND | 44,960 | 33,000 | 7,200 |
| PMP | 1.00% | | | | |
| Tumeric | 0.20% | ND | 38,800 | 34,320 | 30,400 |
| PMP | 1.00% | | | | |
| Natamycin | 0.50% | 34,000 | 16,160 | ND | 7280 |
| PMP | 1.00% | | | | |
| Omega 3 | 0.20% | ND | 16,160 | 10,320 | 7,440 |
| PMP | 1.50% | | | | |
| Nisin | 0.50% | ND | 37,060 | 12,480 | 1,680 |
| PMP | 1.00% | | | | |
| N-acetyl-D-glucosamine | 0.30% | 37,900 | 37,560 | ND | 30,560 |
| PMP | 1.00% | | | | |
| Mehtyl sulfonyl methane (MSM) | 0.30% | 39,840 | 41,200 | ND | 30,400 |
| PMP | 1.00% | | | | |

These results demonstrate that D-glucosamine, potassium sorbate, grapeseed extract, natamycin, omega-3, and nisin degrade the HA over a time frame of 11 months. Additives that are questionable as to degradation of HA were Innovapure, and cynatine. Additives that appear acceptable in that they did not degrade HA were tumeric, N-acetyl-D-glucosamine, methyl sulfonyl methane (MSM), and chondroitin sulfate.

Potential antimicrobial agents were then evaluated for their effectiveness in larger volumes. One liter formulations of HA were prepared as a 1% solution using HA with a molecular weight of approximately 1.8 million Daltons. Immediately after the addition of the HA and before dissolution, the antimicrobial agent was added either alone or in combination. Then, the preparations were mixed until the HA was dissolved. The results of this experiment are shown in Tables 7 and 8.

TABLE 7

Stability of HA gels containing various antimicrobial agents as measured by rheologic viscosity

| | | Viscosity in Centipoise (cP) | | | | | | | |
|---|---|---|---|---|---|---|---|---|---|
| Addition | Conc. | April 2010 | May 2010 | November 2010 | December 2010 | April 2011 | May 2011 | November 2011 | April 2012 | Comments |
| Potassium Benzoate | 0.10% | 21,800 | 14,720 | ND | | | | | | Contamin. |
| Nisin | 0.10% | | | | | | | | | |
| Potassium Sorbate | 0.10% | | | | | | | | | |
| Citric Acid | 0.15% | 18,400 | 600 | ND | 0 | | | | | Dark yellow |
| Potassium Sorbate | 0.10% | | | | | | | | | Degraded |
| | | | | | | | | | | Pungent odor |
| Leucidal | 0.05% | 18,880 | 15,440 | ND | ND | 10,360 | | | | Clear |
| Leucidal | 0.50% | 23,880 | ND | 17,000 | 11,800 | ND | 7,000 | ND | 3,600 | Clear |

The results shown in Table 7 indicate that potassium sorbate, even in combination with other known antimicrobial agents, such as potassium benzoate and Nisin, allows growth of the bioburden in a larger size vessel (1 liter amounts) and produces degradation of the HA molecule. When combined with citric acid, the degradation of the HA molecule is exacerbated producing unacceptable results within one month. Additionally, potassium sorbate produces an unacceptable odor and taste in the HA formulation. At high concentrations, Leucidal (raddish root extract) was acceptable for a period up to 1 year, but by 2 years it led to significant degradation of the HA molecule. The lower concentration of Leucidal appeared to produce satisfactory results.

acceptable antimicrobial activity. Natamycin alone demonstrated some degradation of the HA molecule, but may be able to be used in lower concentrations. A combination of Potassium Benzoate, Zinc Citrate and Calcium Propionate produced acceptable results. No degradation of the HA occurred and the formulation maintained its sterility. There was a small amount of cloudiness and a very small amount of precipitate. However, this can be managed by the formulation process.

The next set of experiments involved preparation of HA solutions in 10 liter volumes. The larger the amount of HA liquid produced, the higher the probability of the antimicrobial agent being unable to control the bioburden. The HA concentration used was 1.0% and the molecular weight was

TABLE 8

Five month stability of HA gels, in 1 liter quantities, containing various antimicrobial agents as measured by rheologic viscosity

| | | Viscosity in Centipoise (cP) | | | | | | |
|---|---|---|---|---|---|---|---|---|
| Addition | Conc. | November 2010 | December 2010 | April 2011 | May 2011 | November 2011 | April 2012 | Comments |
| Citric Acid | 0.15% | 23,160 | ND | 1,840 | 600 | 200 | 0 | Dark yellow, |
| Potassium Sorbate | 0.10% | | | | | | | degraded, pungent odor |
| Potassium Benzoate | 0.1% | | 35,200 | 21,800 | 14,750 | 11,480 | 4,920 | Slightly cloudy |
| Nisin | 0.01% | | | | | | | |
| Potassium Sorbate | 0.1% | | | | | | | |
| Potassium Benzoate | 0.15% | | 23,400 | 22,800 | 20,480 | 19,450 | 19,920 | Cloudy ppt Ppt with |
| Zinc Citrate | 0.30% | | | | | | | crystal |
| Calcium propionate | 0.20% | | | | | | | formation |
| Nisin | 0.50% | | 36,960 | 32,080 | ND | 26,320 | Contam | Cloudy |
| Potassium Sorbate | 0.20% | | 36,800 | 15,600 | ND | 0 | | Dark yellow, degraded, |
| PMP | 1.00% | | | | | | | pungent odor |
| Natamycin | 0.50% | | 34,000 | 25,280 | ND | 17,600 | | Slightly cloudy |

The results shown above in Table 8 again confirm that the combination of citric acid and potassium sorbate is unacceptable as is Potassium Sorbate alone with PMP. The results after only 5 months at room temperature indicated that the formulation had turned a dark yellow color and contained a pungent odor. The taste was also unacceptable. This formulation is not acceptable for use with HA solutions, gels, creams or ointments. Potassium sorbate in combination with Nisin and Potassium Benzoate, which are all otherwise known and acceptable antimicrobial agents, also demonstrated degradation of the HA. Nisin alone did not provide approximately 1 million Daltons. The formulations were prepared by adding each of the non-HA components to sterile distilled water, shaking or swirling until dissolution occurred (where possible), then adding the HA and mixing until the HA was dissolved. HA dissolution took up to 1 week to complete. The control for this experiment was the HA with only PMP. The first samples were removed at 1 month post formulation to assure that all of the HA was dissolved. All formulations were tested for pH at periodic intervals to assure that there were no significant changes in this parameter.

TABLE 9

Eight month stability of HA gels, in 10 liter quantities, containing various potential antimicrobial agents as measured by rheologic viscosity

| | | Viscosity in Centipoise (cP) | | | | | | |
|---|---|---|---|---|---|---|---|---|
| Additives | Conc. | 1 Mo | 2 Mo | 4 Mo | 5 Mo | 6 Mo | 8 Mo | Comments |
| PMP | 1.0% | 2400 pH 6.54 | 2580 | 2770 | 2550 | 2790 | 2750 pH 6.66 | Clear |
| Zn Citrate | 0.15% | 2115 | 2360 | 2160 | 2010 | 3000 | 3840 | Clear |
| Ca Propionate | 0.15% | pH | | | | pH | pH | Sl ppt |
| K Benzoate | 0.15% | 6.42 | | | | 6.50 | 6.48 | |
| Zn Citrate | 0.15% | 1735 | 1870 | 1945 | 1750 | 2105 | 2300 | Clear |
| Ca Propionate | 0.15% | pH | | | | pH | pH | |

TABLE 9-continued Eight month stability of HA gels, in 10 liter quantities, containing various potential antimicrobial agents as measured by rheologic viscosity

| Additives | Conc. | Viscosity in Centipoise (cP) | | | | | | Comments |
|---|---|---|---|---|---|---|---|---|
| | | 1 Mo | 2 Mo | 4 Mo | 5 Mo | 6 Mo | 8 Mo | |
| Grapefruit Seed Extract | 0.01% | 6.73 | | | | 6.55 | 6.60 | |
| Zinc Citrate | 0.3% | 3790 | 3770 | 4090 | 3960 | 4850 | 4580 | Sl |
| Calcium Propionate | 0.2% | pH 6.37 | pH 6.02 | | | pH 6.40 | pH 6.31 | Cloudy |
| Potassium Benzoate | 0.15% | | | | | | | |
| Grapefruit seed extract | 0.03% | | | 1650 | 1650 | 1825 pH 6.52 | 1730 pH 6.45 | Cloudy |
| Zinc Citrate | 0.3% | | | | | | | |
| Zinc Citrate | 0.15% | | | 2870 | 2615 | 2890 pH 6.55 | 3010 pH 6.67 | No ppt Clear |
| Calcium Propionate | 0.15% | | | | | | | |
| Grapefruit seed extract | 0.01% | | | | | | | |
| Grapefruit Seed Extract | 0.01% | | | 3185 | 2730 | 3042 pH 6.58 | 2950 pH 6.52 | No ppt Clear with slight yellow from NAG and MSM |
| Zn Citrate | 0.15% | | | | | | | |
| N-acetyl-D-glucosamine | 0.84% | | | | | | | |
| Methyl sulfonyl methane | 0.51% | | | | | | | |

The results shown in Table 9 indicate that all of the formulations produced acceptable results. At periodic intervals throughout the storage time (at room temperature) samples were removed and tested for purity. This purity testing included inoculating at least 1.0 mL of the formulation onto each of three blood agar plates and incubating them at 37° C. for 3 days and room temperature for a period of 7 more days. No colonies were observed in these tests. The following combinations are, therefore, believed acceptable as antimicrobial agents in HA solutions, gels, creams, and ointments: 1) Zinc Citrate, Calcium Propionate and Potassium Benzoate; 2) Zinc Citrate, Calcium Propionate and Grapefruit Seed Extract; 3) Zinc Citrate, Calcium Propionate and Potassium Benzoate; and 4) Zinc Citrate and Grapefruit Seed Extract. It is noted that when the latter combination was included with N-acetyl-D-glucosamine (NAG) and methyl sulfonyl methane (MSM) as additives, the formulation retained its viscosity and sterility. These combinations may, therefore, be used to support formulations with additional nutritional supplement additives. It is also noted that Zinc Citrate and Grapefruit Seed Extract have their own nutritional supplement values. Zinc is an essential mineral that aids in skin repair, relieves acne, cold sores, colds, ear, and eye problems, improves gum health by removing calculus from the teeth and helps to fight autoimmune and inflammatory diseases such as lupus, arthritis and fibromyalgia. The body does not manufacture zinc on its own, so zinc must be supplied via foods or supplements. Grapefruit Seed Extract is known to help in healing and fighting scar tissue, as well as fighting various diseases such as colds. It is reported to have anti-fungal and anti-cancer activities as well.

This experiment also demonstrates that when zinc citrate is added to formulations that contain additives that normally degrade HA such as Citracidal™ (a brand of grapefruit seed extract), the zinc citrate stabilizes the HA. For instance compare the results in Table 9 with those listed in Table 5. In Table 5 the Citracidal is shown to degrade the HA molecule. However, in Table 9, when combined with zinc citrate, the HA molecule is stabilized (not degraded).

Another experiment was conducted in 10 liter amounts in order to evaluate the ability of PMP to preserve HA formulations to which other supplements (additives) were added. The HA concentration was approximately 0.3% using HA with a molecular weight of approximately 2.5 million Daltons. The formulations were prepared by adding the PMP to sterile distilled water after which the supplements were added individually and mixed until they were all dissolved. After the initial supplement was added, the second supplement was added and the formulation mixed until dissolution of that occurred. After all supplements were added, the HA was added and the entire contents were mixed until the HA was dissolved. This generally required only a couple of days. In this case, the HA with only PMP served as the control.

TABLE 10

Eight month stability of HA gels, in 10 liter quantities, containing various additives in combination with PMP as measured by rheologic viscosity

| Additive | Conc | Viscosity in Centipoise (cP) | | | | | | | Comments |
|---|---|---|---|---|---|---|---|---|---|
| | | Day 0 | 1 Mo | 2 Mo | 4 Mo | 5 Mo | 6 Mo | 8 Mo | |
| HA | 0.31% | 232 | 210 | 239 | 281 | 310 | 599 | 679 | Clear |
| PMP | 0.5% | | | pH | | | pH | | |

TABLE 10-continued

Eight month stability of HA gels, in 10 liter quantities, containing various additives in combination with PMP as measured by rheologic viscosity

| Additive | Conc | Day 0 | 1 Mo | 2 Mo | 4 Mo | 5 Mo | 6 Mo | 8 Mo | Comments |
|---|---|---|---|---|---|---|---|---|---|
| HA | 0.31% | 202 | 176 | 6.66 pH 195 6.85 | 190 | 185 | 6.11 pH 270 6.72 | 371 pH 6.89 | Light yellow and clear |
| PMP | 0.5% | | | | | | | | |
| NAG | 1.0% | | | | | | | | |
| HA | 0.31% | 176 | 148 | 164 pH 6.71 | 166 | 168 | 235 pH 6.90 | 429 pH 7.00 | Light yellow and clear |
| PMP | 0.5% | | | | | | | | |
| NAG | 1.0% | | | | | | | | |
| MSM | 1.0% | | | | | | | | |
| HA | 0.31% | 50 | 43 | ND | ND | 0 | | | Degraded immediately |
| PMP | 0.5% | | | | | | | | |
| NAG | 1.0% | | | | | | | | |
| MSM | 1.0% | | | | | | | | |
| Cynatine | 1.67% | | | | | | | | |
| HA | 0.31% | 152 | 171 | 20 | ND | 0 | | | Degraded rapidly, did not dissolve or disperse |
| PMP | 0.5% | | | | | | | | |
| Omega 3 | 0.2% | | | | | | | | |
| HA | 0.31% | 50 | 43 | 40 | 27 | 23 | | | Degraded immediately, did not dissolve or disperse |
| PMP | 0.5% | | | | | | | | |
| MSM | 1.0% | | | | | | | | |
| NAG | 1.0% | | | | | | | | |
| Omega 3 | 0.2% | | | | | | | | |

The results from Table 10 demonstrate that formulations containing Cynatine along with N-acetyl-D-glucosamine (NAG) and methyl sulfonyl methane (MSM), or omega 3 alone or in combination were unacceptable additives. These produced significant degradation of the HA. Combinations of NAG and MSM were acceptable.

The next experiment was conducted in a 10 liter amount in order to evaluate the ability of zinc citrate alone to act as an antimicrobial agent when added to HA formulations. The HA concentration was approximately 0.3% (3 mg/mL) using HA with a molecular weight of approximately 2.5 million Daltons. The formulations were prepared by adding 0.075% zinc citrate to sterile normal saline (0.9% sodium chloride) after which the HA was added and mixed until it was dissolved. Dissolution of the HA required approximately seven days. Samples were removed for analysis at three month intervals over a two year time frame. Results are presented in Table 11.

A food grade HA with an average molecular weight of 1.5 million Daltons was combined 50:50 with HA having an average molecular weight of 2.5 million Daltons. This was added to 10 liters of water containing zinc citrate at a concentration of 0.1%. Samples were removed as soon as the HA was dissolved and at three month intervals thereafter. The results for 12 months of testing are shown in Table 12.

TABLE 12

Twelve month stability of HA gels, in 10 liter quantities, containing zinc citrate as the antimicrobial agent

| Test | 0 Time | 3 Mo | 6 Mo | 9 Mo | 12 Mo |
|---|---|---|---|---|---|
| Appearance | Clear, Colorless Sl. Viscous | Clear, Colorless Sl. Viscous | Clear, Colorless Sl. Viscous | Clear, Colorless Sl. Viscous | Clear, Colorless Sl. Viscous |
| Purity | 0, 0, 0 | 0, 1, 0 | 0, 0, 0 | 0, 0, 0 | 0, 0, 0 |
| Viscosity LVT 1, Spindle 3, 3 rpm | 18,240 | 17,920 | 18,440 | 18,640 | 18,680 |

TABLE 11

Twenty-four month stability of HA gels, in 10 liter quantities, containing zinc citrate as the antimicrobial agent of HA

| Test | 0 Time | 3 Mo | 6 Mo | 9 Mo | 12 Mo | 18 Mo | 24 Mo |
|---|---|---|---|---|---|---|---|
| Appearance | Clear, Colorless Sl. Viscous | Clear, Colorless Sl. Viscous | Clear, Colorless Sl. Viscous | Clear, Colorless Sl. Viscous | Clear, Colorless Sl. Viscous | Clear, Colorless Sl. Viscous | Clear, Colorless Sl. Viscous |
| Purity | 0, 0, 0 | 0, 0, 0 | 0, 0, 0 | 0, 0, 0 | 0, 1, 0 | 0, 0, 0 | 0, 0, 0 |
| Viscosity LVT 1, Spindle 34, 60 rpm | 301 | 297 | 286 | 292 | 300 | 305 | 307 |
| HA Conc. | 0.32 | 0.33 | 0.31 | 0.32 | 0.31 | 0.32 | 0.33 |
| pH | 6.12 | 6.15 | 6.21 | 6.15 | 6.18 | 6.20 | 6.17 |

TABLE 12-continued

Twelve month stability of HA gels, in 10 liter quantities, containing zinc citrate as the antimicrobial agent

| Test | 0 Time | 3 Mo | 6 Mo | 9 Mo | 12 Mo |
|---|---|---|---|---|---|
| HA Conc. | 1.03 | 1.02 | 1.01 | 1.04 | 1.02 |
| pH | 6.12 | 6.15 | 6.21 | 6.15 | 6.18 |

This experiment demonstrates that zinc citrate is effective as an antimicrobial agent for use in a 1.0% HA solution containing both food grade and cosmetic grade HA.

Although the present disclosure has been described with reference to particular means, materials and embodiments, from the foregoing description, one skilled in the art can easily ascertain the essential characteristics of the present disclosure and various changes and modifications may be made to adapt the various uses and characteristics without departing from the spirit and scope of the present disclosure.

What is claimed:

1. A method of preparing a liquid-based composition, the method comprising:
   adding zinc citrate to water;
   adding hyaluronic acid, or its salt or derivative thereof to the zinc citrate and water;
   dissolving hyaluronic acid, or its salt or derivative thereof, in the combination of the zinc citrate and water;
   wherein the hyaluronic acid, or its salt or derivative thereof, dissolved into the combination of the zinc citrate and water after the zinc citrate was added to the water; and
   forming a solution of the hyaluronic acid, or its salt or derivative thereof, and the zinc citrate.

2. The method of claim 1 further comprising the steps of agitating the zinc citrate and water prior to dissolving the hyaluronic acid, or its salt or derivative thereof, to the combination of the zinc citrate and water.

3. The method of claim 1 further comprising the steps of allowing the combination of zinc citrate, hyaluronic acid, or its salt or derivative thereof, and water to stand for at least one day to dissolve the hyaluronic acid, or its salt or derivative thereof, in the combination of the zinc citrate and water.

4. The method of claim 1, wherein the solution demonstrates microbial growth less than about 10 colony-forming units over about 6 months.

5. The method of claim 1, wherein the solution does not undergo a reduction in viscosity by more than about 50 percent over about 6 months as measured by rheologic viscosity and Centipoise when the composition has an original viscosity of at least 50 Centipoise.

6. The method of claim 1, wherein the molecular weight of the solution is not substantially reduced over about 6 months as measured by rheologic viscosity in Centipoise.

7. The method of claim 1, wherein the solution of hyaluronic acid, or its salt or derivative thereof, and the zinc citrate is a gel.

8. The method of claim 1, wherein the hyaluronic acid, or its salt or derivative thereof, added to the liquid-based composition had a molecular weight of about 100,000 Daltons to about 3 million Daltons.

9. The method of claim 1, further comprising the steps of forming the solution with about 0.001% to about 5% by weight hyaluronic acid, or its salt or derivative thereof; and about 0.0001% to about 50% by weight zinc citrate.

10. A method of preparing a liquid-based composition, the method comprising:
    adding zinc citrate to water;
    adding hyaluronic acid, or its salt or derivative thereof to the water;
    forming a solution of the hyaluronic acid, or its salt or derivative thereof, and the zinc citrate;
    wherein the composition has a viscosity of at least 50 Centipoise as measured by rheologic viscosity.

11. The method of claim 10, further comprising the steps of allowing the combination of zinc citrate, hyaluronic acid, or its salt or derivative thereof, and water to stand for at least one day.

12. The method of claim 10, wherein the solution demonstrates microbial growth less than about 10 colony-forming units over about 6 months.

13. The method of claim 10, wherein the solution of hyaluronic acid, or its salt or derivative thereof, and the zinc citrate is a gel.

14. The method of claim 10, wherein the hyaluronic acid, or its salt or derivative thereof, added to the liquid-based composition had a molecular weight of about 100,000 Daltons to about 3 million Daltons.

15. The method of claim 10, further comprising the steps of forming the solution with about 0.001% to about 5% by weight hyaluronic acid, or its salt or derivative thereof; and about 0.0001% to about 50% by weight zinc citrate.

16. A method of preparing a liquid-based composition, the method comprising:
    adding zinc citrate to water;
    adding hyaluronic acid, or its salt or derivative thereof to the water;
    agitating the combination of zinc citrate, hyaluronic acid, or its salt or derivative thereof, and water;
    allowing the combination of zinc citrate, hyaluronic acid, or its salt or derivative thereof, and water to stand for at least one day;
    forming a solution of the hyaluronic acid, or its salt or derivative thereof, and the zinc citrate.

17. The method of claim 16, wherein the zinc citrate is added to the water prior to adding the hyaluronic acid, or its salt or derivative thereof is added to the water.

18. The method of claim 16, further comprising the steps of intermittently mixing the combination of zinc citrate, hyaluronic acid or its salt or derivative thereof, and the water while allowing the combination of zinc citrate, hyaluronic acid, or its salt or derivative thereof, and water to stand for at least one day.

19. The method of claim 16, wherein the composition has a viscosity of at least 50 Centipoise as measured by rheologic viscosity.

* * * * *